United States Patent [19]
Vandemoortele et al.

[11] Patent Number: 5,569,227
[45] Date of Patent: Oct. 29, 1996

[54] DISPOSABLE ABSORBENT HYGIENE ARTICLE HAVING WAISTBAND POCKETS IMPROVING THE SEALING

[75] Inventors: Philippe Vandemoortele, Lille; André Leroy, Mouvaux, both of France

[73] Assignee: Peadouce, Linselles, France

[21] Appl. No.: 162,110

[22] PCT Filed: Jun. 10, 1992

[86] PCT No.: PCT/FR92/00525

§ 371 Date: Jan. 11, 1994

§ 102(e) Date: Jan. 11, 1994

[87] PCT Pub. No.: WO92/22271

PCT Pub. Date: Dec. 23, 1992

[30] Foreign Application Priority Data

Jun. 12, 1991 [FR] France .................................. 91 07164

[51] Int. Cl.[6] .................................................. A61F 13/15
[52] U.S. Cl. ........................ 604/382; 604/385; 604/385.2
[58] Field of Search ............................... 604/382, 385.1, 604/385.2, 393–399; 156/164, 229

[56] References Cited

U.S. PATENT DOCUMENTS 4,662,877 5/1987 Williams .

FOREIGN PATENT DOCUMENTS

| | | |
|---|---|---|
| 0109126A1 | 5/1984 | European Pat. Off. . |
| 0203712A1 | 12/1986 | European Pat. Off. . |
| 0264238A1 | 4/1988 | European Pat. Off. . |
| 0376022A3 | 8/1991 | European Pat. Off. . |
| 2161059 | 1/1986 | United Kingdom . |

Primary Examiner—John G. Weiss
Assistant Examiner—Karin M. Reiche
Attorney, Agent, or Firm—Burns, Doane, Swecker & Mathis, L.L.P.

[57] ABSTRACT

A sanitary article of the type comprising an external backing sheet which is impervious to liquids, an absorbing pad, an internal cover sheet pervious to liquids and two side flaps with elastic elements. An additional sheet is arranged under the cover sheet overlapping one transverse edge of the pad, and is connected by gluing to the cover sheet which presents, over the additional sheet, a transverse cutting. An elastic element is passed along the edge of the cutting in order to form a waist sealing pocket open at the cutting.

14 Claims, 5 Drawing Sheets

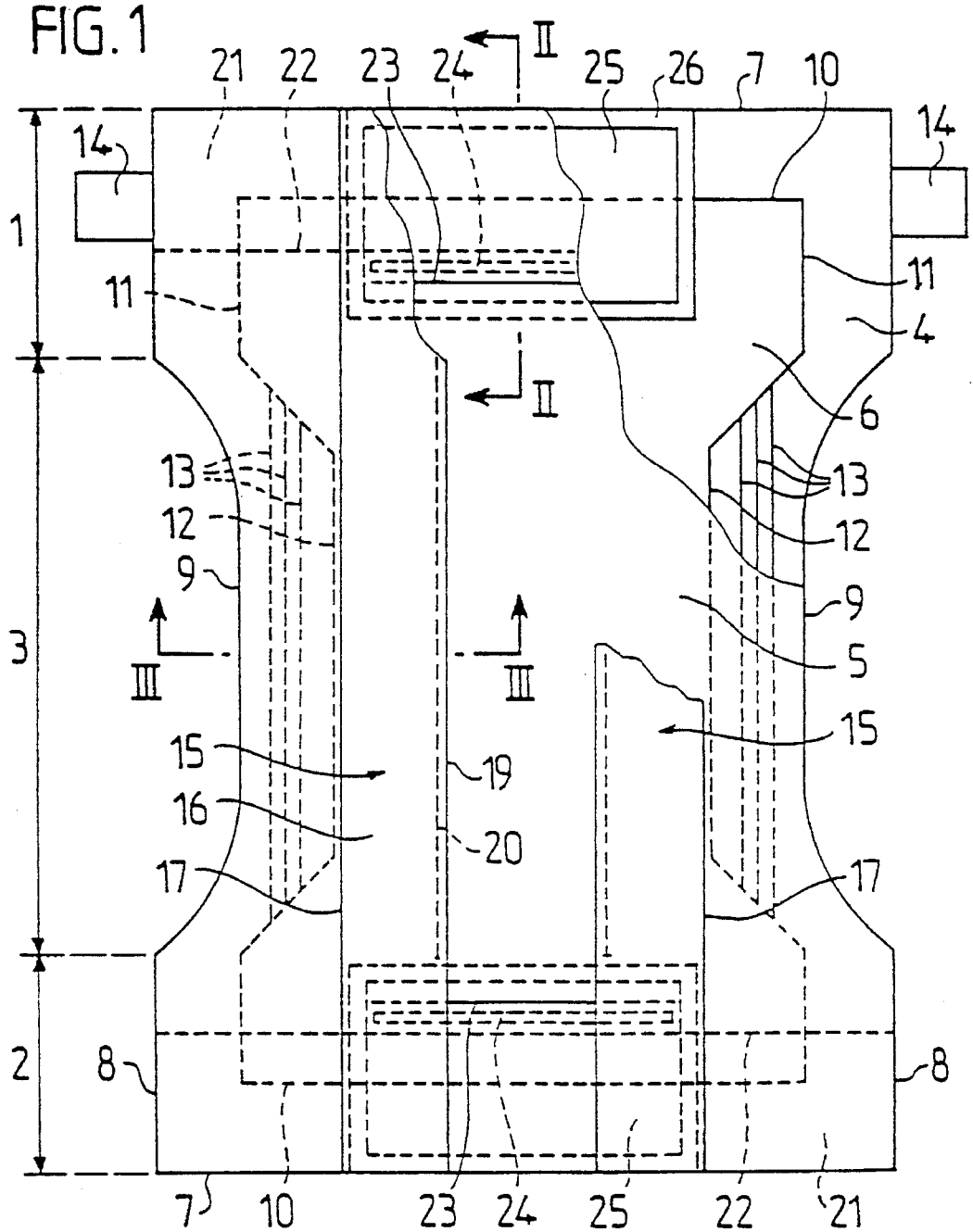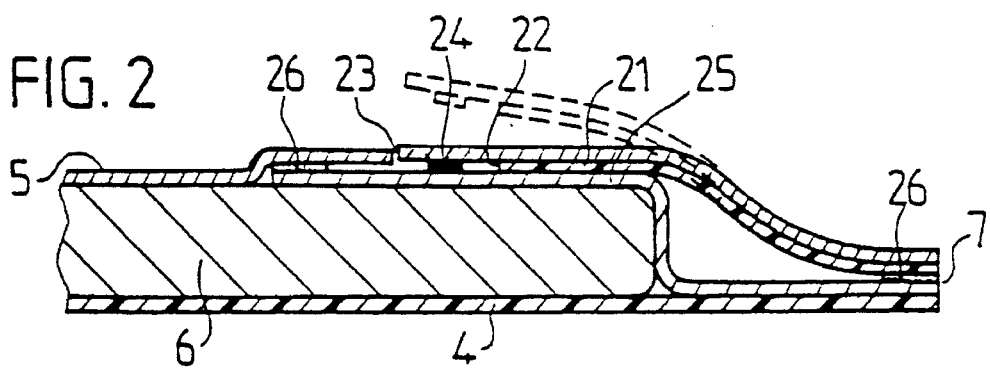

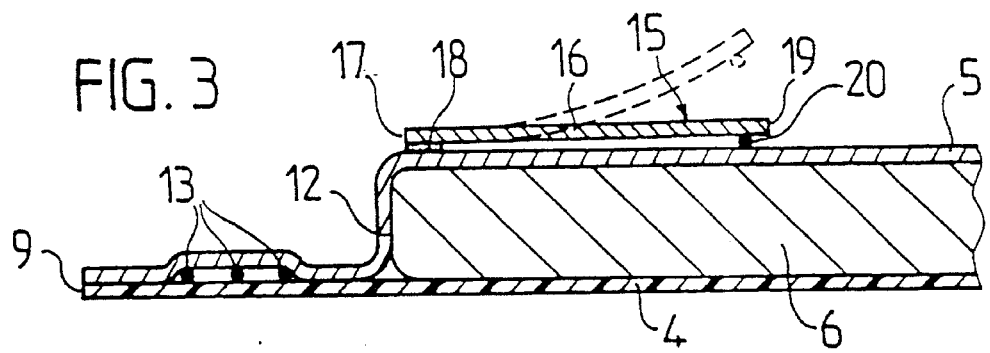
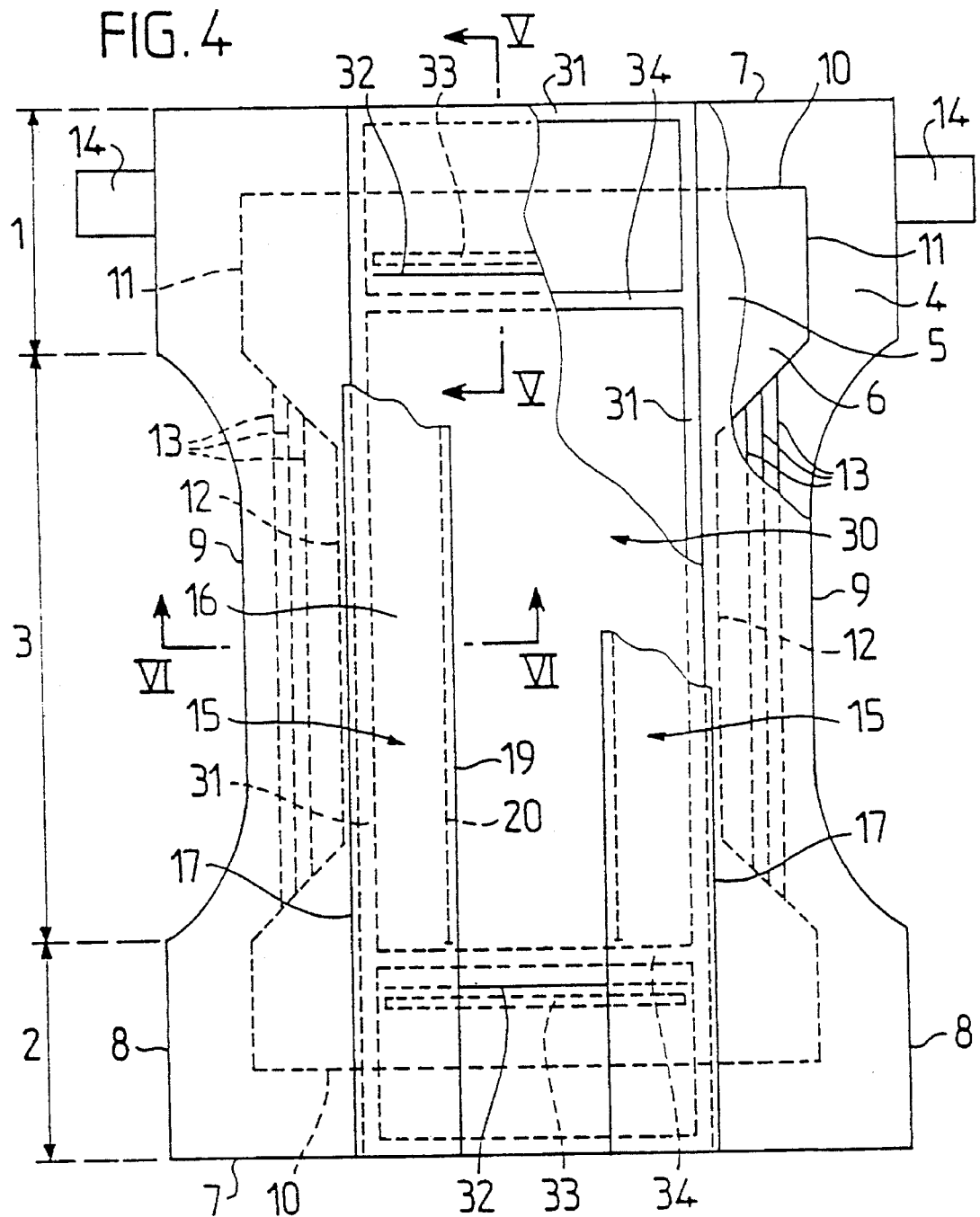

DISPOSABLE ABSORBENT HYGIENE ARTICLE HAVING WAISTBAND POCKETS IMPROVING THE SEALING

This application is a 371 of an International application filed under Patent Cooperation Treaty bearing application Ser. No. PCT/FR 92/00525, filed 10 Jun. 1992 and published as WO-92/22271, 23 Dec. 1992 which application lists the United States as a designated country.

The present invention relates to disposable absorbent hygiene articles, especially napkin pilches, of the type comprising an external supporting sheet impermeable to liquids, an internal covering sheet, an absorbent pad arranged between said sheets, longitudinally elastic elements fastened in the tensioned state to said supporting sheet on the outside of the longitudinal edges of the absorbent pad, and fastening means for closing the hygiene article around the waist of a user.

BACKGROUND OF THE INVENTION

To improve the general sealing of these hygiene articles in the crotch zone and the effect of the containment of urine and fecal substances, this being achieved even in the case of violent diarrheal defecations often encountered in infants, it has already been proposed, for example by Patent Application GB-A-2,161,059, to provide additionally, on the internal face of the covering sheet, two transversely spaced lateral tabs or flaps extending substantially along the longitudinal edges of the hygiene article. These flaps each have a proximal part joined to the covering sheet and a distal part having tensioned longitudinal elastic elements.

By virtue of their tensioned elastic elements, these lateral flaps are permanently laid against the user's skin, whatever the movements made by the latter, and this is not always true of the longitudinal elastic elements fastened to the external supporting sheet, particularly on account of the presence of the absorbent pad and of the rigidity and thickness of the pad. However, this improvement only relates to the transverse or lateral sealing (at the crotch) and not the longitudinal sealing (at the waistband).

The attempts to improve the sealing of the waistband by the provision of an elasticised waistband and/or of an impermeable transverse strip covering the transverse edge of the absorbent pad have not been entirely satisfactory.

It has already been proposed, in Patent Applications EP-A-2,264,238 and EP-A-0,376,022, to provide on a hygiene article of the type comprising internally two elastic lateral tabs or flaps, at least in the vicinity of one transverse edge of the article, a transverse element forming a waistband pocket extending between said flaps, being arranged either above or below said flaps. This element is fastened transversely in a tensioned state to the underlying parts of the hygiene article by means of its transverse edge corresponding to the transverse edge of the hygiene article and over all or some of its longitudinal edges, whilst its other transverse edge remains free, thus allowing the element to open in the manner of a pocket at the location of this internal free transverse edge. However, these pocket elements are not entirely satisfactory insofar as they do not afford sufficient sealing, especially with regard to migrations of liquid in the direction of the waistband. Moreover, the production of a hygiene article having such pocket elements is relatively complicated and therefore entails an appreciable increase in the cost of the article.

Finally, the U.S. Pat. No. 4,662,877 makes known a napkin pilch, the covering sheet of which is covered over its entire length with a rectangular additional sheet permeable to liquids, of reduced width, fastened to the covering sheet along its four sides and provided with a central orifice of general rectangular shape, the opposite longitudinal edges of which are fitted with tensioned elastic elements. These tensioned longitudinal elastic elements lift the additional sheet from the covering sheet and from the underlying absorbent pad along the longitudinal edges of said orifice, thus forming types of lateral barriers. However, this lifting effect is limited by reason, among other things, of the reduced length of these elastic elements. The same is true of the lifting, hence of the waistband-pocket effect, of the transverse edges of the said orifice under the tension of the longitudinal elastic elements.

The object of the present invention is to improve the hygiene articles of the type with lateral tabs or flaps and with a waistband pocket or waistband pockets, in such a way as to improve, in general terms, the longitudinal sealing effect, that is to say at the location of the waistband, in particular from the point of view of the migration of liquids. The object of the invention is also to provide a napkin pilch of this type which, whilst being of higher efficiency, can be produced at a reduced cost.

SUMMARY OF THE INVENTION

The disposable absorbent hygiene article according to the invention, especially a napkin pilch, has a substantially rectangular general shape with opposite longitudinal edges and opposite transverse edges. This article comprises, from the outside inwards, a supporting sheet impermeable to liquids, an absorbent pad arranged on the internal face of the supporting sheet, and a covering sheet. The dimensions of the absorbent pad are smaller than those of the supporting sheet, and the covering sheet covers the internal face of the absorbent pad and of the supporting sheet and is joined to the latter over the periphery of the absorbent pad. The hygiene article comprises, furthermore, longitudinal elastic elements fastened in the tensioned state to the supporting sheet on the outside of the lateral edges of the absorbent pad. Moreover, the hygiene article comprises two transversely spaced lateral flaps arranged on the internal face of the covering sheet substantially along the longitudinal edges of the hygiene article, said flaps each having a proximal part joined to the covering sheet and a distal part having tensioned longitudinal elastic elements. Furthermore, the hygiene article comprises fastening means in the vicinity of one of its transverse edges, for closing the hygiene article around the waist of a user in such a way that the hygiene article defines a front part and a rear part corresponding respectively to the two end zones near said opposite transverse edges of the hygiene article and a crotch part corresponding to the intermediate zone located between said end zones. According to the invention, the hygiene article comprises, furthermore, underneath said lateral flaps, an additional sheet permeable to liquids and extending from at least one of said transverse edges at least over the corresponding transverse edge of the absorbent pad. Of the two sheets formed by the covering sheet and said additional sheet, a first, which is furthest from the absorbent pad, comprises, above the absorbent pad, in the vicinity of said transverse edge of the absorbent pad, a transverse cutout extending between said proximal parts of the lateral flaps. Said first sheet is equipped, furthermore, with a tensioned transverse elastic element extending along said cutout on the side confronting the corresponding transverse edge of the hygiene article. Moreover, said sheet is fastened to the second of said two sheets at least along said transverse edge of the hygiene article and in the extension of the two ends of said transverse elastic element, in such a way that the said first sheet forms a sealing waistband pocket open at the location of said cutout.

Said additional sheet can be arranged between the absorbent pad and the covering sheet and form said second sheet.

Said additional sheet can also be arranged on the internal face of said covering sheet and thus form said first sheet.

Said additional sheet can either be continuous, that is to say extend in the longitudinal direction of the hygiene article from one transverse edge of this article to the other, or be limited to the front part and/or the rear part of the hygiene article.

The fixing of the first sheet to the second sheet can advantageously be carried out by a U-shaped adhesive bond along the transverse edge of the first sheet corresponding to the transverse edge of the hygiene article and along the longitudinal edges of the first sheet over all or some of the length of these edges.

Preferably, this fixing is carried out by means of a rectangular adhesive bond according to a transverse line extending along the transverse edge of the hygiene article, according to two longitudinal lines extending along the longitudinal edges of the first sheet and according to a transverse line extending along the transverse cutout of the first sheet on the side remote from the corresponding transverse edge of the hygiene article.

The part of the first sheet located between said transverse cutout and the corresponding transverse edge of the hygiene article is preferably impermeable.

According to one embodiment of the invention, the additional sheet forming said first sheet and extending over the entire length of the hygiene article is fixed to the covering sheet over the entire length of the hygiene article by means of two longitudinal connecting lines set back relative to the longitudinal edges of the additional sheet, tensioned elastic elements being fixed along said longitudinal edges of the additional sheet. Thus, the parts of said additional sheet which are located between said longitudinal connecting lines and said longitudinal edges form the tabs or flaps improving the transverse sealing.

In this case, the additional sheet permeable to liquids can advantageously be coated or treated so as to be impermeable or hydrophobic in the region of said flaps.

Referring to the accompanying diagrammatic drawings, several illustrative and non-limiting embodiments of a hygiene article according to the invention will be described hereafter in more detail; in the drawings:

BRIEF DESCRIPTION OF THE DRAWINGS

FIG. 1 is a view of the internal face of a napkin pilch according to the invention arranged flat also depicting a partial cut away view;

FIG. 2 is a partial section on a larger scale according to II—II of FIG. 1;

FIG. 3 is a partial section on a larger scale according to III—III of FIG. 1;

FIG. 4 is a view of the internal face of another embodiment of a napkin pilch according to the invention, arranged flat also depicting a partial cut away view;

DETAILED DESCRIPTION OF THE INVENTION

Figure 5:
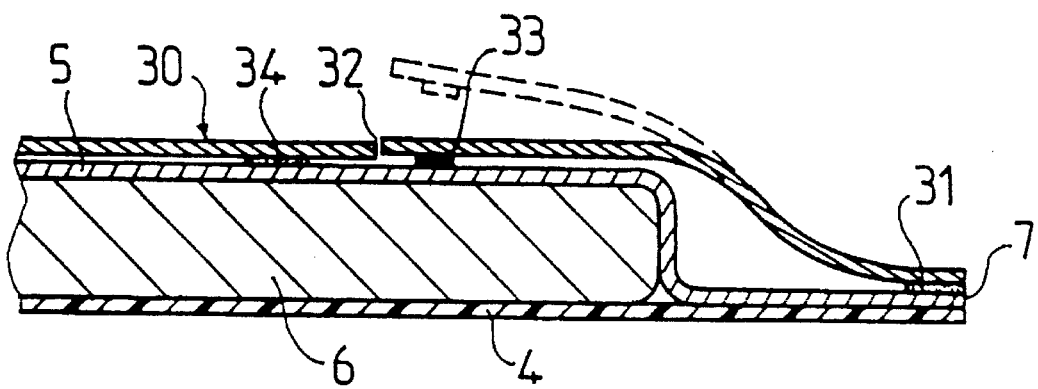
FIG. 5 is a partial section on a larger scale according to V—V of FIG. 4.

The disposable napkin pilch, as illustrated in FIGS. 1 to 3, is a so-called anatomical or hourglass-shaped napkin pilch having a general rectangular shape with two opposite lateral cutouts making it possible to define, in the longitudinal direction of the napkin pilch, a rear part 1 corresponding to one longitudinal end zone, a front part 2 corresponding to the other longitudinal end zone, and a crotch part 3 corresponding to the intermediate zone of the napkin pilch. In the crotch part 3, the napkin pilch has a smaller width than in the front part 1 and in the rear part 2.

The general structure of the napkin pilch according to FIGS. 1 to 3 corresponds to that of conventional napkin pilches, comprising from the outside inwards, that is to say from bottom to top in FIGS. 2 and 3, an external supporting sheet 4 impermeable to liquids, an internal covering sheet 5 permeable to liquids, and an absorbent pad 6 arranged between the two sheets 4 and 5.

According to FIG. 1, the two sheets 4 and 5 have the same size and the same shape, namely a general rectangular shape with two opposite straight transverse edges 7 and two opposite longitudinal edges 8, each comprising an indentation 9 substantially in the middle of its length, thus giving the two sheets 4 and 5 their hourglass shape, the indentations 9 defining the crotch part 3 of reduced width.

The absorbent pad 6 arranged between the two sheets 4 and 5 and likewise hourglass-shaped has a size reduced in relation to that of the sheets 4 and 5 and is centred relative to these sheets 4 and 5 in such a way that its two straight transverse edges 10 and its two longitudinal edges 11, each provided with an indentation 12, are respectively set back inwards in relation to the corresponding edges 7 and 8 of the two sheets 4 and 5.

The napkin pilch comprises, furthermore, in a way known per se, two longitudinal elastic elements 13, each consisting, in the example illustrated, of the three spaced elastic strands fixed in the tensioned state to the external sheet 4, at least in the crotch part 3, between the bottom of the indentations 12 of the absorbent pad 6 and the bottom of the indentations 9 of the sheets 4 and 5.

Two adhesive fasteners 14 are provided in a way known per se on the rear part 1, for the purpose of closing the napkin pilch around the waist of a user, the fasteners 14 then interacting with the front part 2 of the napkin pilch.

It should be noted that the means for fixing the internal sheet 5 to the external sheet 4 around the absorbent pad 6, the means for fixing the absorbent pad 6 to the sheet 4 and the means for fixing the elastic elements 13 to the external sheet 4 are not shown, these means known per se possibly consisting, for example, of lines or coatings of adhesive.

The internal sheet 5 carries on its internal face, that is to say the face which can be seen in FIG. 1, two lateral sealing or barrier flaps or tabs 15. As emerges from FIG. 3, each tab 15 is formed from a tape 16 of a sheet-like material, permeable or impermeable to liquids, extending over the entire length of the napkin pilch. The tape 16 is joined at its proximal end, corresponding to its external longitudinal edge 17, by means of a line of adhesive 18 to the covering sheet 5, namely, in the example illustrated, in a position slightly set back inwards relative to the bottom of the indentation 12 of the absorbent pad 6. At its distal end 19 corresponding to its internal longitudinal edge, the tape 16 carries an elastic element 20 fastened, preferably by adhesive bonding, in a tensioned state to the tape 16 over the middle part of the length of the latter corresponding to the crotch part 3.

These lateral flaps or tabs 15, known per se, are intended for improving the barrier and sealing effect in the lateral direction, the function of the tensioned elastic elements 20 being to lift the flaps 16 in relation to the covering sheet 5, as represented by dashes in FIG. 3, and lay them against the user's skin, so as to give them some independence from the remaining parts of the napkin pilch and particularly from the absorbent pad 6, so that the tabs 15 can follow the movements of the user, whilst remaining laid against the skin of the latter.

Moreover, a transverse strip 21 impermeable to liquids is provided on the covering sheet 5 in the region of each transverse edge 7 of the napkin pilch. In the example illustrated, the strip 21 consists of an impermeable sheet lining the covering sheet 5 on the face confronting the absorbent pad 6, this strip 21 extending over the entire width of the sheet 5 and having, in the longitudinal direction of the napkin pilch, a dimension such that the strip 21 overlaps the absorbent pad 6, its internal edge 22 being set back inwards relative to the corresponding transverse edge 10 of the pad 6.

As emerges from FIGS. 1 and 2, the covering sheet 5 comprises, both in the rear part 1 and in the front part 2 of the napkin pilch, a transverse cutout 23 extending in the middle position over a length slightly smaller than the transverse distance separating the external edges 17 of the two lateral flaps 15 from one another. Each of the cutouts 23 is offset inwards relative to the internal edge 22 of the impermeable strip 21 of the covering sheet 5, in such a way that the cutout 23 is located above the pad 6.

Furthermore, the covering sheet 5 carries, on its internal face confronting the absorbent pad 6, in each of the parts 1 and 2 of the napkin pilch, a transverse elastic element 24 extending along said cutout 23 between the latter and the internal edge 22 of the impermeable transverse strip 21, the elastic element 24 being fixed in the tensioned state to the sheet 5.

Finally, a liquid-permeable sheet portion 25 extends, in each of the two parts 1 and 2 of the napkin pilch, in the middle of the width of the latter, underneath the covering sheet 5, from the corresponding transverse edge 7 of the napkin pilch inwards over the corresponding transverse edge 10 of the absorbent pad 6 and beyond the corresponding transverse cutout 23 of the covering sheet 5. The sheet portion 25 has, in the transverse direction of the napkin pilch, a dimension slightly smaller than the distance separating the external longitudinal edges 17 of the two lateral flaps 15 from one another.

The rectangular sheet portion 25 is fixed over its entire periphery to the covering sheet 5 by a rectangular adhesive bond 26.

In the embodiment illustrated in FIGS. 4 to 6, there is once again an hourglass-shaped napkin pilch with a rear part 1, a front part 2 and crotch part 3 of reduced width. This napkin pilch is likewise formed from an external supporting sheet 4 impermeable to liquids, from an internal covering sheet 5 permeable to liquids, from an absorbent pad 6 arranged between the two sheets 4, 5 in such a way that its edges 10, 11, 12 are set back relative to the corresponding edges 7, 8, 9 of the two sheets 4 and 5, from longitudinal elastic elements 13 arranged on either side of the absorbent pad 6 in the crotch zone, from adhesive fasteners 14 and from two lateral flaps or tabs 15 consisting of tapes 16 fixed in the vicinity of their external longitudinal edge 17, corresponding to their proximal end, to the covering sheet 5 by means of a line of adhesive 18 and carrying in the vicinity of their internal longitudinal edge 19, forming their distal end, a longitudinal elastic element 20 fixed in the tensioned state.

In this embodiment, a liquid-permeable sheet strip 30, having a width slightly smaller than the distance separating from one another, transversely to the length of the napkin pilch, the two lines of adhesive 18 by means of which the lateral flaps 15 are fixed to the covering sheet 5, extends in the middle position over the entire length of the napkin pilch on the internal face of the covering sheet 5. The strip 30 is fixed over its entire periphery by means of a rectangular adhesive bond 31 to the covering sheet 5 and comprises, in the rear part 1 and in the front part 2, above the absorbent pad 6, in each case a transverse cutout 32 extending transversely to the length of the napkin pilch over a length slightly smaller than the width of the strip 30.

Each transverse cutout 32 of the strip 30 has extending along it, on the side confronting the corresponding transverse edge 7 of the napkin pilch, a transverse elastic element 33 fixed in the tensioned state to the face of the strip 30 confronting the absorbent pad 6 and, on the opposite side, a transverse strip of adhesive 34 meeting and completing the rectangular adhesive bond 31 extending over the entire periphery of the strip 30.

Figure 6:
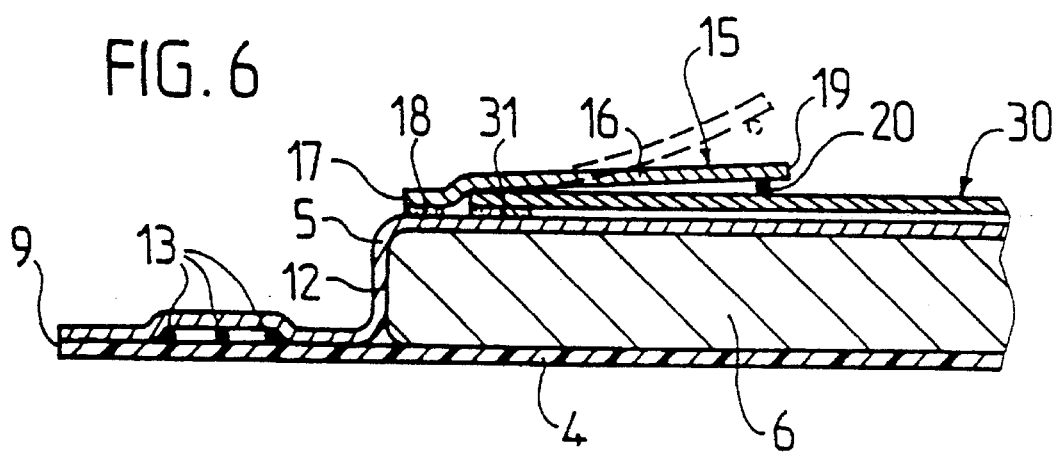
FIG. 6 is a partial section on a larger scale according to VI—VI of FIG. 4.
Figure 7:
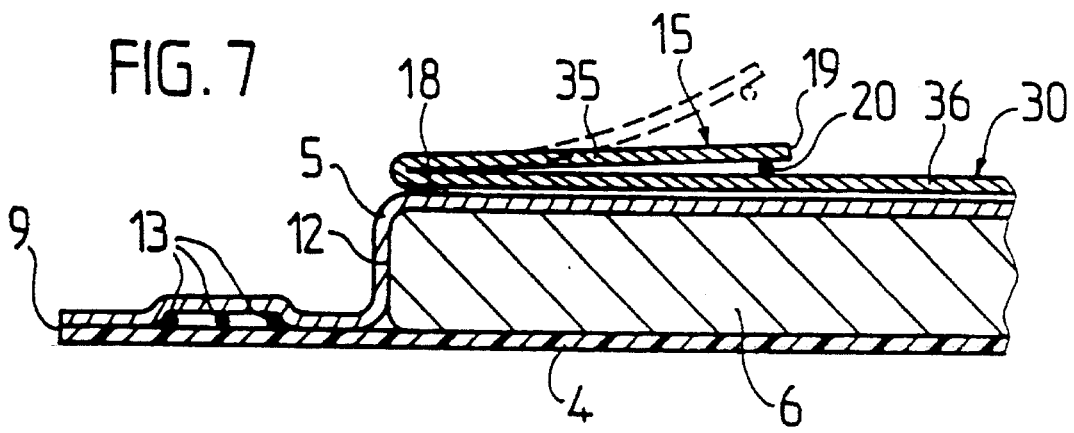
FIG. 7 is a section, corresponding to that of FIG. 6, of an alternative version in which the lateral flaps and waistband pockets are formed from one and the same liquid-permeable sheet.

The version according to FIG. 7 differs from the embodiment according to FIGS. 4 to 6 only in that the two lateral flaps 15 are produced in one piece with the sheet strip 30 which covers the covering sheet 5 over the entire length of the napkin pilch. For this purpose, the sheet strip 30 has a width larger than the width of the absorbent pad 6 in the crotch part 3 (transverse distance separating the bottoms of the indentations 12 of the pad 6), and the two lateral parts 35 of the strip 30, which are located outside the longitudinal lines of adhesive 18 by means of which the middle part 36 of the strip 30 is fixed to the covering sheet 5 above the absorbent pad 6, are folded inwards to form lateral sealing flaps 15 equipped with longitudinal elastic elements 20 tensioned at their distal end 19.

The remaining part of the napkin pilch corresponds exactly to the embodiment of FIGS. 4 to 6.

Consequently, in the embodiment of FIG. 7, the lateral flaps 15 improving sealing at the crotch and the pockets improving sealing at the waistband consist of one and the same element, namely the strip 30.

In the two embodiments according to FIGS. 4 to 6 and according to FIG. 7, in which the transverse cutouts 32 are made in a strip 30 extending over the covering sheet 5 for the entire length of the napkin pilch, the strip 30, consisting of a liquid-permeable material, for example a nonwoven, can be made impermeable or hydrophobic in the region of the waistband pockets, for example by coating or another treatment.

Such an impermeable or hydrophobic coating or treatment could also be provided, in the embodiment of FIG. 7, on the parts 35 of the strip which form the lateral flaps 15.

Similarly, the tapes 16 forming the lateral flaps 15 in the embodiments according to FIGS. 1 to 3 and 4 to 6 can advantageously consist of nonwoven tapes made hydrophobic or impermeable.

Furthermore, in the embodiment of FIGS. 1 to 3, the covering sheet 5, in which the transverse cutouts 23 are made, could be made impermeable or hydrophobic by a coating or treatment in the region of the waistband pockets, preferably over the entire width of the napkin pilch.

Figure 8:
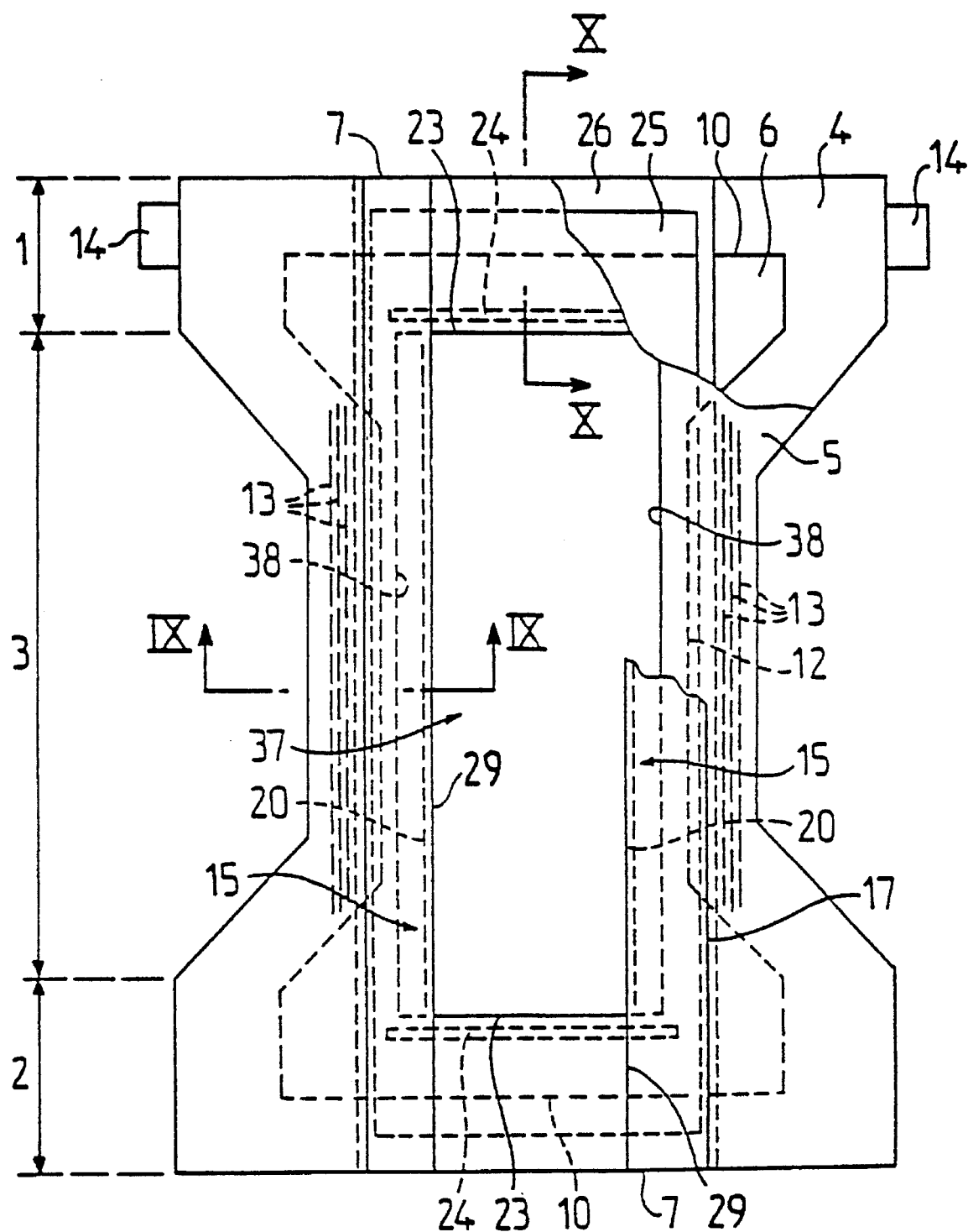
FIG. 8 is a view of the internal face of yet another embodiment of a napkin pilch according to the invention, arranged flat also depicting a partial cut away view.
Figure 9:
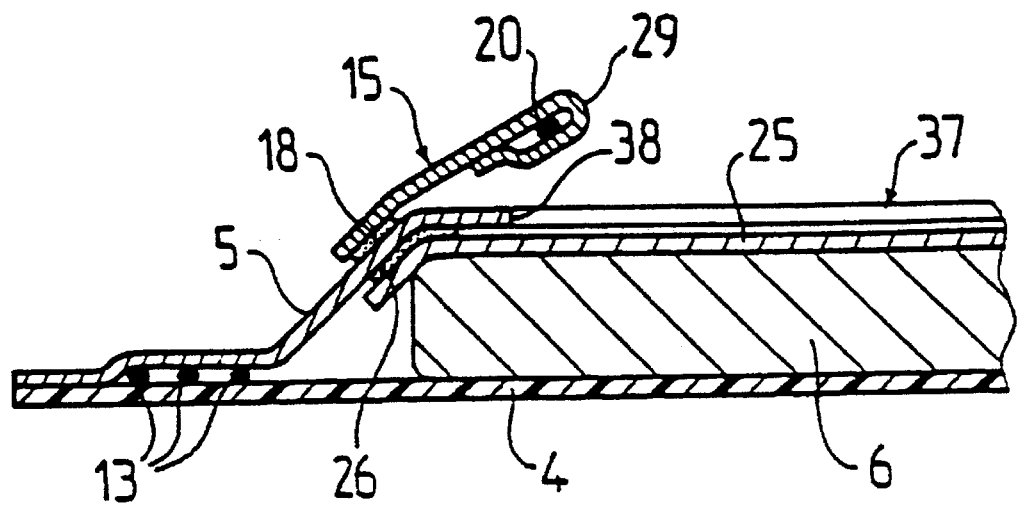
FIGS. 9 and 10 are sections on a larger scale according to IX—IX and according to X—X of FIG. 8.
Figure 10:
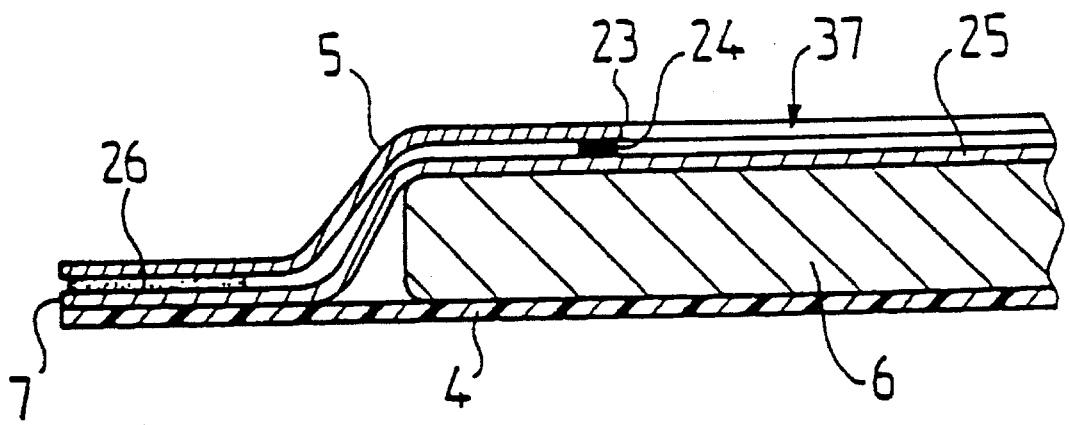

The napkin pilch of the embodiment according to FIGS. 8 to 10 comprises a supporting sheet 4 with longitudinal elastic elements 13, an absorbent pad 6, a covering sheet 5 which completely covers the supporting sheet 4 and the pad 6, and two lateral flaps 15. Moreover, a tape 25 having a width slightly larger than the width of the absorbent pad 6 in the crotch part 3 extends between the covering sheet 5 and the pad 6, over the entire length of the napkin pilch, between the two opposite transverse edges 7 of the latter. This tape, consisting of a liquid-permeable material, for example a nonwoven, is fixed over its entire periphery to the covering sheet 5, for example by means of a rectangular strip of adhesive 26.

The covering sheet 5, produced from a flexible material, such as a nonwoven, hydrophobic or preferably liquid-impermeable material, comprises in the central position an orifice 37 of general rectangular shape, elongate in the longitudinal direction of the napkin pilch and of a width smaller than the width of the pad 6 in the crotch part 3. This orifice 37 is defined by two transverse cutouts or edges 23 which are clearly set back relative to the transverse bonding zones 26 and which are each equipped with a tensioned transverse elastic element 24, and by two opposite longitudinal cutouts or edges 38 which join the ends of said edges 23 and along which are fixed, for example by means of strips of adhesive 18, the two lateral flaps 15 which extend over the entire length of the napkin pilch and which each carry a tensioned elastic element 20 in the vicinity of their distal part 29.

Thus, the two elasticated transverse edges 23 of the orifice 37 of the covering sheet 5 define two sealing waistband pockets which extend between said edges 23 and the strips of adhesive 26 and which, in combination with the two lateral flaps 15, form a sealing pocket preventing leaks of liquids or solids over the entire periphery of the napkin pilch.

It is expedient to note that the transverse cutouts or edges 23, instead of being straight, could also be curved, particularly with an outward convexity, thus giving the orifice 37 a shape rounded at its longitudinal ends.

Furthermore, instead of producing the orifice 37 by means of two transverse cutouts and two longitudinal cutouts joining the ends of the transverse cutouts, it would be possible to make in the covering sheet an I-shaped cutout, with two transverse cutouts and a single middle longitudinal cutout, and to fold the two tabs thus formed towards the top or towards the bottom. In this case, the two tabs can preferably be elasticated in the vicinity of their folding lines. It is then possible to omit the lateral flaps 15, the elasticated tabs being capable of performing the function of the flaps, that is to say of producing lateral sealing barriers relatively independent of the underlying absorbent pad.

Although the examples shown illustrate napkin pilches for children or for incontinent adults, the invention can also be used for other hygiene articles having the same general structure. Whatever the nature of these hygiene articles, they can likewise comprise, within the scope of the invention, a single sealing waistband pocket either at the front or the rear.

Moreover, the invention can also be used for hygiene articles which are not hourglass-shaped, but, for example, are of rectangular shape.

Another possibility applicable to all the embodiments illustrated involves lining the tape portion 25 or the strip 30 with an elastic impermeable sheet in the zone or zones to be impermeable, and utilising the elasticity of this sheet, preferably of the heat-activatable type, to replace the attached elastic element 24 or 33.

We claim:

1. A disposable absorbent hygiene article having a general rectangular shape with first and second opposite longitudinal edges and first and second opposite transverse edges and comprising from outside inward:

a supporting sheet impermeable to liquids having first and second opposite longitudinal edges, first and second opposite transverse edges, an external face and an internal face;

an absorbent pad having first and second opposite longitudinal edges, first and second opposite transverse edges, an external face, and an internal face, said absorbent pad being arranged on the internal face of said supporting sheet, said pad being smaller in size than said supporting sheet;

a covering sheet having first and second opposite longitudinal edges, first and second opposite transverse edges, an external face and an internal face, said covering sheet covering the internal face of said absorbent pad and of the supporting sheet and being joined to the supporting sheet around said longitudinal and transverse edges of the absorbent pad;

longitudinal elastic elements fastened in a tensioned state to said supporting sheet transversely outside the first and second opposite longitudinal edges of said absorbent pad;

fastening means provided in the vicinity of said first transverse edge of the hygiene article, in order to close the latter around a user's waist in such a way that the hygiene article defines a rear part and a front part corresponding respectively to two end zones near said opposite first and second transverse edges of said hygiene article and a crotch part corresponding to an intermediate zone located between said end zones;

two transversely spaced lateral flaps arranged on the internal face of the covering sheet substantially along said first and second longitudinal edges of said hygiene article, each of said flaps having a proximal part joined to the covering sheet and a distal part having a tensioned longitudinal elastic element; and a first additional sheet permeable to liquids having first and second opposite transverse edges, first and second opposite longitudinal edges, an external face and an internal face, said first additional sheet being arranged between the absorbent pad and the covering sheet and extending from said first transverse edge of the hygiene article at least over the first transverse edge of the absorbent pad which is closest to said first transverse edge of the hygiene article;

wherein said covering sheet further comprises:

a) a first transverse cutout above the absorbent pad between the proximal parts of said lateral flaps, in the vicinity of said first transverse edge of the absorbent pad, and having a first side confronting said first transverse edge of the hygiene article and a second opposite side; and b) a first tensioned transverse elastic element extending along said first cutout on said first side thereof confronting said first transverse edge of the hygiene article and having two ends, wherein said covering sheet is fastened to the first additional sheet at least along said first transverse edge of the hygiene article and adjacent the two ends of said first transverse elastic element, in order to form a sealing waistband pocket open at the location of said first transverse cutout.

2. The hygiene article of claim 1, further comprising a second additional sheet permeable to liquids having first and second opposite transverse edges, first and second opposite longitudinal edges, an external face and an internal face, said second additional sheet being arranged between the absorbent pad and the covering sheet and extending from said second transverse edge of the hygiene article at least over the second transverse edge of the absorbent pad which is closest to said second transverse edge of the hygiene article;

wherein said covering sheet further comprises:
c) a second transverse cutout above the absorbent pad between the proximal parts of said lateral flaps, in the vicinity of said second transverse edge of the absorbent pad, having a first side confronting said second transverse edge of the hygiene article and a second opposite side; and,
b) a second tensioned transverse elastic element extending along said second cutout on said first side thereof confronting said second transverse edge of the hygiene article and having two ends, wherein said covering sheet is fastened to the second additional sheet at least along said second transverse edge of the hygiene article and adjacent the two ends of said second transverse elastic element in order to form a sealing waistband pocket open at the location of said second transverse cutout.

3. The hygiene article of claim 2, wherein said first and second transverse cutouts have ends and said covering sheet further comprises first and second longitudinal cutouts joining the ends of said first and second transverse cutouts to one another, in such a way that said transverse cutouts and said longitudinal cutouts define a central orifice of general rectangular shape in said covering sheet.

4. The hygiene article of claim 1, wherein part of said covering sheet located between said first transverse cutout and said first transverse edge of the hygiene article is hydrophobic or impermeable to liquids.

5. The hygiene article of claim 1, wherein said fastening of the covering sheet to the first additional sheet comprises fixing said covering sheet to said first additional sheet by means of at least a U-shaped adhesive bond line formed by a transverse adhesive line extending along the first transverse edge of the hygiene article and two longitudinal lines extending respectively along at least some of the longitudinal edges of said first additional sheet.

6. The hygiene article of claim 5, wherein said fixing of the covering sheet to the first additional sheet includes an additional transverse adhesive line extending along said first cutout on said second opposite side thereof.

7. A disposable absorbent hygiene article having a general rectangular shape with first and second opposite longitudinal edges and first and second opposite transverse edges and comprising, from outside inward:

a supporting sheet impermeable to liquids having first and second opposite longitudinal edges, first and second opposite transverse edges, an external face and an internal face;

an absorbent pad having first and second opposite longitudinal edges, first and second opposite transverse edges, an external face and an internal face, said absorbent pad being arranged on the internal face of said supporting sheet, said pad being smaller in size than said supporting sheet;

a covering sheet permeable to liquids having first and second opposite longitudinal edges, first and second transverse edges, an external face and an internal face, said covering sheet covering the internal face of said absorbent pad and of the supporting sheet and being joined to the supporting sheet around said longitudinal and transverse edges of the absorbent pad;

longitudinal elastic elements fastened in a tensioned state to said supporting sheet transversely outside of the first and second opposite longitudinal edges of said absorbent pad;

fastening means provided in the vicinity of said first transverse edge of the hygienic article, in order to close the latter around a user's waist in such a way that the hygiene article defines a rear part and a front part corresponding respectively to two end zones near said opposite first and second transverse edges of said hygiene article and a crotch part corresponding to an intermediate zone located between said end zones;

two transversely spaced lateral flaps arranged on the internal face of the covering sheet substantially along said first and second longitudinal edges of said hygiene article, each of said flaps having a proximal part joined to the covering sheet and a distal part having a tensioned longitudinal elastic element; and a first sheet portion having a first and second opposite longitudinal edges, first and transverse edge, an external face and an internal face, said first sheet portion being arranged on the internal face of said covering sheet and extending from said first transverse edge of the hygiene article to at least over the first transverse edge of the absorbent pad which is closest to said first transverse edge of the hygiene article;

wherein said first sheet portion further comprises:
a) a first transverse cutout above the absorbent pad between the proximal parts of said lateral flaps, in the vicinity of said first transverse edge of the absorbent pad, and having a first side confronting said first transverse edge of the hygiene article and a second opposite side; and,
b) a first tensioned transverse elastic element extending along said first cutout on said first side thereof confronting said first transverse edge of the hygiene article and having two ends, wherein said first sheet portion is fastened to said covering sheet at least along said first transverse edge of the hygiene article and adjacent the two ends of said first transverse elastic element, in order to form a sealing waistband pocket open at the location of said first transverse cutout.

8. The hygiene article of claim 7 further comprising a second sheet portion having a first opposite longitudinal edges, first and second transverse edge, an external face and an internal face, said second sheet portion being arranged on the internal face of said covering sheet portion and extending from said second transverse edge of the hygiene article to at least over the second transverse edge of the absorbent pad which is closest to said second transverse edge of the hygiene article;

wherein said second sheet portion further comprises:
a) a second transverse cutout above the absorbent pad between the proximal parts of said lateral flaps, in the vicinity of said second transverse edge of the absorbent pad, and having a first side confronting said second transverse edge of the hygiene article and a second opposite side; and, b) a second tensioned transverse elastic element extending along said second cutout on said first side thereof confronting said second transverse edge of the hygiene article and having two ends, wherein said second additional sheet is fastened to said covering sheet at least along said second transverse edge of the hygiene article and adjacent the two ends of said second transverse elastic element, in order to form a sealing waistband pocket open at the location of said second transverse cutout.

9. The hygiene article of claim 8, wherein said first and second sheet portions are formed by a single sheet extending from said first transverse edge to said second transverse edge of the hygiene article.

10. The hygiene article of claim 9, wherein said single sheet is permeable to liquids, is fixed to the covering sheet over the entire length of the hygiene article by means of two longitudinal bonding lines set back relative to longitudinal edges of said single sheet, parts of said single sheet which are located between said longitudinal bonding lines and said longitudinal edges of said single sheet forming said lateral flaps.

11. The hygiene article of claim 10, wherein said single sheet is coated or treated so as to be impermeable or hydrophobic in the parts forming said flaps.

12. The hygiene article of claim 7, wherein part of said first sheet portion located between said first transverse cutout and said first transverse edge of the hygiene article is hydrophobic or impermeable to liquids.

13. The hygiene article of claim 7, wherein said fastening of the first sheet portion to the covering sheet comprises fixing said first additional sheet portion to said covering sheet by means of at least a U-shaped adhesive bond line formed by a transverse adhesive line extending along the first transverse edge of the hygiene article and two longitudinal lines extending respectively along at least some of the longitudinal edges of said covering sheet.

14. The hygiene article of claim 7, wherein said fixing of the first sheet portion to the covering sheet includes an additional transverse adhesive line extending along said first cutout on said second opposite side thereof.

* * * * *